United States Patent
Honda et al.

(10) Patent No.: US 11,933,725 B2
(45) Date of Patent: Mar. 19, 2024

(54) METHOD FOR ESTIMATING SULFUR COMPONENT CONCENTRATION IN GASOLINE

(71) Applicants: TOYOTA JIDOSHA KABUSHIKI KAISHA, Toyota (JP); National University Corporation Okayama University, Okayama (JP)

(72) Inventors: Akihiro Honda, Gotemba (JP); Hideki Fukano, Okayama (JP)

(73) Assignees: Toyota Jidosha Kabushiki Kaisha, Toyota (JP); National University Corporation Okayama University, Toyota (JP)

(*) Notice: Subject to any disclaimer, the term of this patent is extended or adjusted under 35 U.S.C. 154(b) by 764 days.

(21) Appl. No.: 17/092,437

(22) Filed: Nov. 9, 2020

(65) Prior Publication Data
US 2021/0156797 A1 May 27, 2021

(30) Foreign Application Priority Data
Nov. 21, 2019 (JP) .................................. 2019-210427

(51) Int. Cl.
*G01N 21/41* (2006.01)
*B01J 38/04* (2006.01)
(Continued)

(52) U.S. Cl.
CPC .......... *G01N 21/4133* (2013.01); *B01J 38/04* (2013.01); *G01N 1/4022* (2013.01);
(Continued)

(58) Field of Classification Search
CPC ... B01J 38/04; G01N 21/4133; G01N 1/4022; G01N 1/44; G01N 33/287; G01N 2001/4027; G01N 2201/06113
(Continued)

(56) References Cited

U.S. PATENT DOCUMENTS 6,849,239 B2 * 2/2005 Morris ............... G01N 33/0031
422/50
7,428,838 B2 * 9/2008 Gugaratshan ...... G01N 33/0011
73/23.31
(Continued)

FOREIGN PATENT DOCUMENTS

CA      2239548 A1 * 12/1997 ............. G01N 21/00
CN   102507497 A      6/2012
(Continued)

OTHER PUBLICATIONS

V.A. Vinokurov, et al., "Detergent Additives for Motor Gasolines and Their Quantitative Determination", Additives and Lubricants, Oil Refining and Petrochemistry, 2010, pp. 21-26.
(Continued)

*Primary Examiner* — Patricia L. Hailey
(74) *Attorney, Agent, or Firm* — Finnegan, Henderson, Farabow, Garrett & Dunner, LLP (57) ABSTRACT

A method is provided that allows the sulfur component concentration in gasoline to be estimated to high precision. The measuring method of the disclosure is a method of measuring the concentration of sulfur components in gasoline that contains sulfur components and aromatic components. The measuring method of the disclosure comprises: (A1) removing a portion of the gasoline by gasification to lower the proportion of the aromatic component concentration with respect to the sulfur component concentration in the gasoline, (A2) measuring values related to the refractive index of the gasoline, and (A3) measuring the sulfur component concentration in the gasoline based on the values related to the refractive index.

7 Claims, 3 Drawing Sheets

(51) Int. Cl.
*G01N 1/40* (2006.01)
*G01N 1/44* (2006.01)
*G01N 33/28* (2006.01)

(52) U.S. Cl.
CPC ............ *G01N 1/44* (2013.01); *G01N 33/287* (2013.01); *G01N 2001/4027* (2013.01); *G01N 2201/06113* (2013.01)

(58) Field of Classification Search
USPC ......... 502/5, 6, 34; 702/24; 73/23.31, 61.41, 73/61.48
See application file for complete search history.

(56) References Cited

U.S. PATENT DOCUMENTS

| | | | | |
|---|---|---|---|---|
| 7,520,163 | B2* | 4/2009 | Kinkade, Jr. | ........ G01N 33/287 73/61.41 |
| 8,156,787 | B2* | 4/2012 | Asanuma | ............ G01N 33/287 73/23.31 |
| 2003/0193662 | A1* | 10/2003 | DiFoggio | ........... G01N 21/3577 356/128 |
| 2005/0069455 | A1* | 3/2005 | Staphanos | ........... G01N 33/287 436/119 |
| 2010/0095741 | A1* | 4/2010 | Otsuki | ............... G01N 33/0042 73/23.31 |
| 2012/0174656 | A1* | 7/2012 | Rebinsky | ............ G01N 33/287 73/61.41 |
| 2015/0033709 | A1* | 2/2015 | Norton | ................ G01M 15/102 73/23.31 |
| 2016/0097758 | A1* | 4/2016 | Ikeya | ..................... B60K 15/03 73/23.31 |
| 2019/0391126 | A1 | 12/2019 | Namekawa et al. | |
| 2020/0072147 | A1* | 3/2020 | Lee | ........................... F02P 5/15 |

FOREIGN PATENT DOCUMENTS

| | | | | | |
|---|---|---|---|---|---|
| JP | 62-009169 | U | | 1/1987 | |
| JP | 62-091840 | A | | 4/1987 | |
| JP | S6291840 | A | * | 4/1987 | ............ G01N 21/27 |
| JP | 2001-050893 | A | | 2/2001 | |
| JP | 2001-303937 | A | | 10/2001 | |
| JP | 2006-348091 | A | | 12/2006 | |
| JP | 2010101801 | A | * | 5/2010 | ............ G01N 21/41 |
| JP | 2012-251963 | A | | 12/2012 | |
| JP | 2015-232522 | A | | 12/2015 | |
| JP | 2017-020946 | A | | 1/2017 | |
| JP | 6413047 | B1 | | 10/2018 | |

OTHER PUBLICATIONS

B.V. Belyanin, et al., "Technical Analysis of Oil Products and Gas", $2^{nd}$ Edition, trans. and add. Publishing House, Chemistry, Leningrad, 1970, pp. 150-152.

N.G. Konrad, et al., "Development of a Formula for Sports Gasoline", Chemical Technology and Biotechnology, 2017, N2, pp. 149-162.

A.V. Anisimova, et al., "Oxidative Desulfurization of Hydrocarbon Raw Materials", Russian Chemical Journal (Journal of the Russian Chemical Society Named After D.I. Mendeleev), 2008, vol. LII, N4, pp. 32-40.

* cited by examiner

METHOD FOR ESTIMATING SULFUR COMPONENT CONCENTRATION IN GASOLINE

FIELD

The present disclosure relates to a method for estimating the concentration of sulfur components in gasoline.

BACKGROUND

Methods for measuring a variety of liquid and gaseous components are known in the prior art. Examples of such methods include chromatographic methods and infrared spectroscopy. Other methods are known that use optical fiber sensors to measure the refractive indexes of liquids or gases, allowing target substances to be estimated.

PTL 1 discloses a method for sensing gases in gasoline, the method employing an optical fiber device using optical fibers as the gas sensor.

The optical fiber device described in PTL 1 is an optical fiber device comprising a sensor unit in the form of an optical fiber composed of a waveguide, and an optical fiber A and optical fiber B composed of a core and cladding, which are each optically connected to one or the other end of the sensor unit and situated on one side and the other side of the sensor unit, wherein the waveguide of the sensor unit is made of the same material as the core of the optical fiber A and optical fiber B, the dimension of the sensor unit in the radial direction is larger than the dimension of the core of the optical fiber A and the dimension of the core of the optical fiber B, and the sensor unit has at least one outer surface that is completely covered with an adsorbent. According to this same publication, the components in a target substance can be detected based on the amount of Goos-Hanchen shift during total reflection at the boundary between the optical fiber and the adsorbent that is to adsorb the target substance, which is disposed on the outer peripheral side of the optical fiber sensor.

CITATION LIST

Patent Literature

[PTL 1] Japanese Unexamined Patent Publication No. 2017-20946

SUMMARY

Technical Problem

Exhaust gas produced by combustion of fuel such as gasoline in an internal combustion engine such as an automobile gasoline engine contains components such as carbon monoxide (CO), hydrocarbons (HC), and nitrogen oxides ($NO_X$). Vehicles with internal combustion engines are therefore usually provided with exhaust gas purification catalyst apparatuses for purification of such components, whereby the components are essentially decomposed by the exhaust gas purifying catalysts mounted in the exhaust gas purification catalyst apparatuses.

Since gasoline contains sulfur components such as benzothiophene, exhaust gas produced by combustion of gasoline also contains sulfur oxides such as $SO_X$ in addition to the components mentioned above. Such sulfur oxides adhere onto or stored by the exhaust gas purifying catalyst, thus lowering the exhaust gas purification performance of the exhaust gas purifying catalyst, i.e. causing catalyst poisoning.

The present inventors have studied a recovery procedure in which the accumulated amount of sulfur oxides discharged from an internal combustion engine is estimated based on the sulfur component concentration in gasoline, and the sulfur oxide is removed from the exhaust gas purifying catalyst when the estimated amount exceeds a constant value.

The present inventors also studied a method of estimating the concentration of sulfur components in gasoline wherein an optical fiber device such as disclosed in PTL 1 is used to measure the refractive index of the gasoline in order to estimate the sulfur component concentration in the gasoline.

However, the present inventors have found that the refractive index of gasoline is greatly affected not only by the sulfur component concentration in gasoline but also by the concentration of aromatic components, and that the concentration of sulfur components and aromatic components in the gasoline differs significantly depending on the period in which the gasoline is acquired, such that it is difficult to estimate the sulfur component concentration in gasoline to high precision simply by measuring the refractive index of the gasoline.

It is therefore an object of this disclosure to provide a method that allows the sulfur component concentration in gasoline to be estimated to high precision.

Solution to Problem

The present inventors have found that this object can be achieved by the following means.

<Aspect 1>

A method for estimating the concentration of sulfur components in gasoline that contains sulfur components and aromatic components, wherein the method comprises:

(A1) removing a portion of the gasoline by gasification to lower the proportion of the aromatic component concentration with respect to the sulfur component concentration in the gasoline, (A2) measuring values related to the refractive index of the gasoline, and (A3) estimating the sulfur component concentration in the gasoline based on the values related to the refractive index.

<Aspect 2>

The method according to aspect 1, wherein in step (A2), an optical fiber device which:

has a sensor unit composed of a multimode fiber that runs through the gasoline, and has an incoming light fiber and outgoing light fiber composed of single-mode fibers, that are optically connected to the incoming light end and outgoing light end of the sensor unit, respectively, wherein the sensor unit and the cores of the incoming light fiber and outgoing light fiber are made of the same material, and the diameter of the sensor unit is larger than the diameters of the cores of the incoming light fiber and outgoing light fiber, is used to irradiate the sensor unit with a laser from the incoming light fiber side and to measure the wavelength of the irradiated laser from the outgoing light fiber side, measuring the values related to the refractive index based on the measured wavelength.

<Aspect 3>

The method according to aspect 1 or 2, wherein in step (A1), the gasoline is heated to gasify a portion of the gasoline.

<Aspect 4>

The method according to aspect 2, wherein in step (A1), the sensor unit interior is irradiated with a laser from the incoming light fiber side to heat the gasoline and gasify a portion of the gasoline.

<Aspect 5>

The method according to any one of aspects 1 to 4, wherein the sulfur components comprise dimethylthiophene, dibenzothiophene, benzothiophene or any combination of the same.

<Aspect 6>

The method according to any one of aspects 1 to 5, wherein the aromatic components comprise toluene.

<Aspect 7>

A method for recovering an exhaust gas purifying catalyst that purifies exhaust gas emitted by an internal combustion engine in which gasoline is combusted, wherein the method comprises:

(A) estimating the sulfur component concentration in the gasoline by the method according to any one of aspects 1 to 6, (B) estimating the estimated accumulated amount of sulfur oxides in the exhaust gas emitted by the internal combustion engine, based on the sulfur component concentration, and (C) recovering the exhaust gas purifying catalyst from the sulfur oxide-derived poisons when the estimated accumulated amount of discharged sulfur oxides is above a threshold value.

Advantageous Effects of Invention

According to the disclosure it is possible to provide a method that allows the sulfur component concentration in gasoline to be estimated to high precision.

DESCRIPTION OF EMBODIMENTS

Embodiments of the disclosure will now be explained in detail. The disclosure is not limited to the embodiments described below, however, and various modifications may be implemented within the scope of the gist thereof.

<Method for Estimating Sulfur Component Concentration>

The estimating method of the disclosure is a method for estimating the concentration of sulfur components in gasoline that contains sulfur components and aromatic components. The estimating method of the disclosure comprises the following steps (A1) to (A3):

(A1) removing a portion of the gasoline by gasification to lower the proportion of the aromatic component concentration with respect to the sulfur component concentration in the gasoline, (A2) measuring values related to the refractive index of the gasoline, and (A3) estimating the sulfur component concentration in the gasoline based on the values related to the refractive index.

Without being limited to any particular principle, it is believed that the principle by which the sulfur component concentration in gasoline can be estimated to high precision by the method of the disclosure is as follows.

Presumably, the refractive index of gasoline is greatly affected not only by the sulfur component concentration in gasoline but also by the aromatic component concentration in gasoline.

The saturated vapor pressure of toluene, which is the major aromatic component in gasoline, is 2.93 kPa at 20° C., while the saturated vapor pressure of benzothiophene, which is the main sulfur component in gasoline, is very low, being 1.33 Pa at 20° C. When gasoline is gasified, therefore, the aromatic components are more easily gasified than the sulfur components in the gasoline. For the alkane components as the main components of gasoline, the saturated vapor pressure of octane, for example, is 1.33 kPa at 20° C., and therefore when the method of the disclosure is applied for gasoline, the aromatic components and alkane components gasify more readily than the sulfur components in the gasoline.

Figure 1:
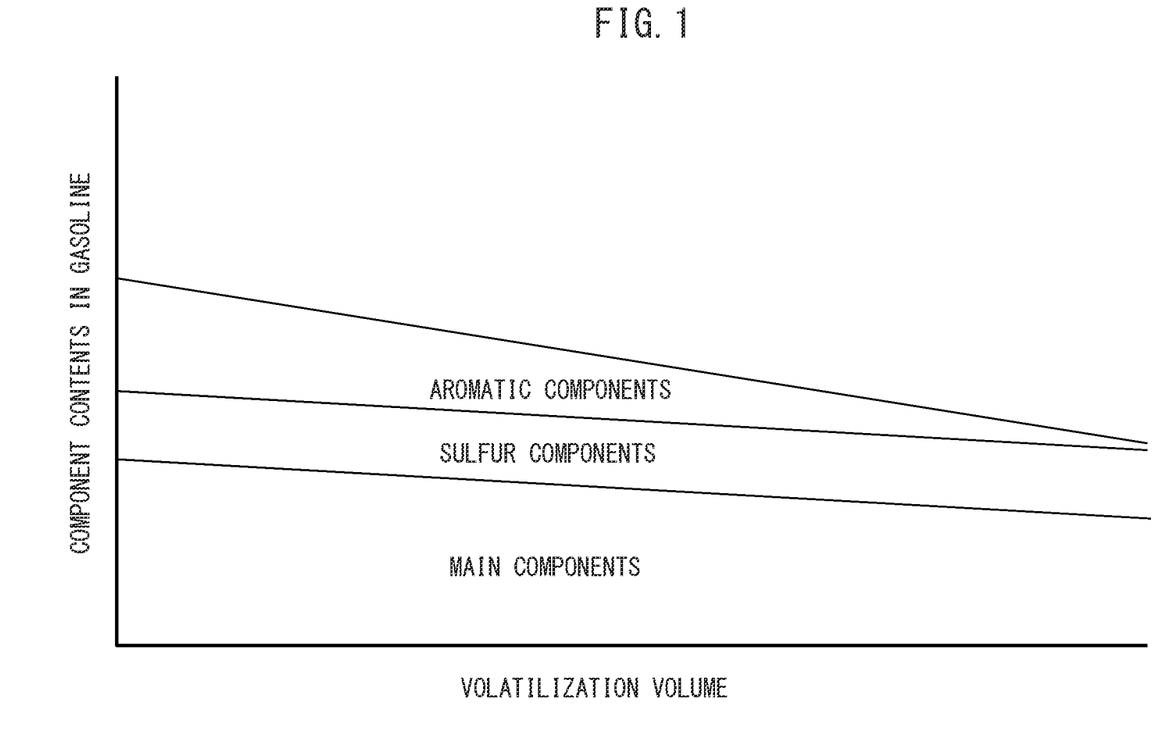
FIG. 1 is a graph illustrating the relationship between gasoline gasification rate (vol %) and the main component, sulfur component and aromatic component concentrations (vol %) in gasoline.

This will be explained in detail in regard to gasoline. As shown in FIG. 1, gasification of gasoline causes gasification of the aromatic components, thereby lowering the aromatic component content of the gasoline. The sulfur components, on the other hand, have very low saturated vapor pressure compared to the other components and undergo almost no gasification, such that the sulfur component content in the gasoline is virtually unchanged.

When the gasoline is gasified, therefore, the aromatic component concentration in the gasoline is lowered and the aromatic components contribute less to the refractive index of the gasoline, whereas the sulfur component concentration in gasoline increases, resulting in greater contribution of the sulfur components to the refractive index of the gasoline.

Thus, if the values related to the refractive index of the gasoline are measured after lowering the proportion of the aromatic component concentration with respect to the sulfur component concentration in gasoline by gasification of a portion of the gasoline, it is possible to improve estimation precision for the sulfur component concentration in gasoline.

<Gasoline>

The estimating method of the disclosure is carried out with gasoline containing sulfur components and aromatic components.

The sulfur components in gasoline are compounds that contain sulfur atoms, examples of which include dimethylthiophene, dibenzothiophene, benzothiophene, and combinations of the same, although with no particular limitation to these.

The aromatic components in gasoline include toluene, for example, but may also include other aromatic compounds.

The gasoline to be used in the estimating method of the disclosure is a liquid. Because of the high saturated vapor pressure of sulfur components, the sulfur component concentration in gasoline vapor is expected to differ considerably from the sulfur component concentration in liquid gasoline. Therefore, the estimation precision for the sulfur component concentration in gasoline may be lower when the values related to the refractive index of gasoline vapor are measured. The estimating method of the disclosure is carried out for liquid gasoline and is therefore less susceptible to this issue.

<Step A1>

In step A1, the proportion of the aromatic component concentration with respect to the sulfur component concentration in gasoline is lowered by removing a portion of the gasoline by gasification.

The gasoline used in step A1 may be gasified to between 1.0 vol % and 25.0 vol %. The gasoline may also be gasified to 1.0 vol % or more, 2.0 vol % or more, 5.0 vol % or more, or 8.0 vol % or more, and 25.0 vol % or less, 20.0 vol % or less, 15.0 vol % or less, or 10.0 vol % or less. Since a greater degree of gasoline gasification allows more of the aromatic components in the liquid gasoline to be gasified, it can increase the estimation precision for the sulfur component concentration. However, a greater degree of gasification of gasoline results in consumption of more gasoline for estimation of the sulfur component concentration in the gasoline, thus leading to greater energy loss.

The method of gasifying a portion of the gasoline may be any desired method capable of gasifying gasoline, and for example, it may be gasification of the gasoline by allowing it to stand at ordinary temperature, or gasification by heating.

<Step A2>

In step A2 the values related to the refractive index of gasoline are measured.

The values related to the refractive index, referred to here, include the value of the refractive index itself, but may also include the basic values used to calculate the refractive index. For example, the wavelength shift may be measured when using an apparatus of the specific type used in the estimating method described below.

Step A2 may employ any method that allows the values related to the refractive index of liquid gasoline to be measured. For the values related to the refractive index, examples of methods for measuring the refractive index itself include, but are not limited to, the minimum deviation method, the Abbe or Pulfrich critical angle method, or the V-block method. Step A2 may also be carried out using an apparatus of the specific type used in the estimating method described below.

Measurement of the values related to the refractive index for liquid gasoline is preferably carried out at a temperature for low gasification of liquid gasoline, but it may also be carried out at ordinary temperature or at above ordinary temperature. The temperature of the liquid gasoline during measurement of the values related to the refractive index for liquid gasoline may be 0° C. to 50° C. The temperature of the liquid gasoline during measurement of the values related to the refractive index for liquid gasoline may also be 0° C. or more, 10° C. or more, or 20° C. or more, and 50° C. or less, 40° C. or less or 30° C. or less.

<Step A3>

In step A3, the sulfur component concentration in gasoline is estimated based on the values related to the refractive index.

Estimation of the sulfur component concentration in gasoline may be estimation using specific numerical values in units of vol %, mass % or mol %, or it may be estimation using the magnitude relationship against a threshold value based on these same units.

The sulfur component concentration in gasoline can be calculated using a mathematical expression representing the relationship between refractive index and sulfur component concentration according to formula (3) in the reference example, using an aromatic component concentration of 0 vol % in the gasoline (assuming a constant aromatic component concentration, i.e. assuming the aromatic components to be essentially gasified), and substituting in the measured refractive index.

The sulfur component concentration in gasoline may be estimated by establishing threshold values for the values related to the refractive index, and determining whether or not the values are above the threshold values and also within the threshold values, to estimate whether the concentration is above the predetermined concentration or within the predetermined concentration. In this case, the threshold values may be theoretical values or measured values for the values related to the refractive index of the gasoline, at the predetermined sulfur component concentration. For example, the measured values can be determined by carrying out step A1 and step A2 for gasoline having a known sulfur component concentration.

<Specific Estimating Method of the Disclosure>

In the estimating method of the disclosure, steps A1 and A2 may be carried out by the following step A1' and step A2', respectively, using the following apparatus as an example.

<Measuring Apparatus>

An example of a measuring apparatus that can be used in the estimating method of the disclosure is an optical fiber device that has a sensor unit composed of a multimode fiber that runs through the gasoline, and has an incoming light fiber and outgoing light fiber composed of single-mode fibers, that are optically connected to the incoming light end and outgoing light end of the sensor unit, respectively, wherein the sensor unit and the cores of the incoming light fiber and outgoing light fiber are made of the same material, and the diameter of the sensor unit is larger than the diameters of the cores of the incoming light fiber and outgoing light fiber.

The optical fiber device may also be the optical fiber device described in PTL 1, for example.

(Sensor Unit)

The sensor unit is composed of a multimode fiber. A multimode fiber is an optical fiber that allows light propagating through an optical fiber to propagate separately in multiple modes. The multimode fiber in the sensor unit does not have a cladding.

The material of the sensor unit may be any desired material that can be used as a core material for an optical fiber, or it may be composed of the same material as the cores of the incoming light fiber and outgoing light fiber. In this case there will be no difference in refractive index between the incoming light fiber and the sensor unit, and between the sensor unit and the outgoing light fiber, so that light passing through the optical fiber device will be trapped inside the core without leaking at the boundary between the incoming light fiber and sensor unit or at the boundary between the sensor unit and outgoing light fiber.

The diameter of the sensor unit is larger than the diameters of the cores of the incoming light fiber and outgoing light fiber. Strong diffraction is thus generated in the light directed from the incoming light fiber onto the sensor unit, and diffracted light produced in the sensor unit is focused by interference at the core of the outgoing light fiber, resulting in highly efficient light propagation from the sensor unit to the outgoing light fiber.

The sensor unit passes through the gasoline, or in other words, the sensor unit is in direct contact with the liquid gasoline. During total reflection at the sensor unit, variation in the phase of the light, known as Goos-Hanchen shifting, takes place in the diffracted light passing through the sensor unit, and therefore light propagating through the center section of the sensor unit undergoes phase variation by the degree of repetition of total reflection, reaching the fiber unit at the output end. Since the phase variation in light due to Goos-Hanchen shifting depends on the refractive index of the sensor unit and the refractive index of the gasoline surrounding the sensor unit, the refractive index of the gasoline can be calculated by measuring the wavelength of light at which the phase just matches at the core of the outgoing light fiber, as a value related to the refractive index.

(Incoming Light Fiber and Outgoing Light Fiber)

The incoming light fiber is composed of a single-mode fiber, and it is optically connected to the incoming light end of the sensor unit. The outgoing light fiber is likewise composed of a single-mode fiber, and it is optically connected to the outgoing light end of the sensor unit.

A single-mode fiber is an optical fiber allowing light propagating through an optical fiber to propagate in a single mode.

Figure 2:
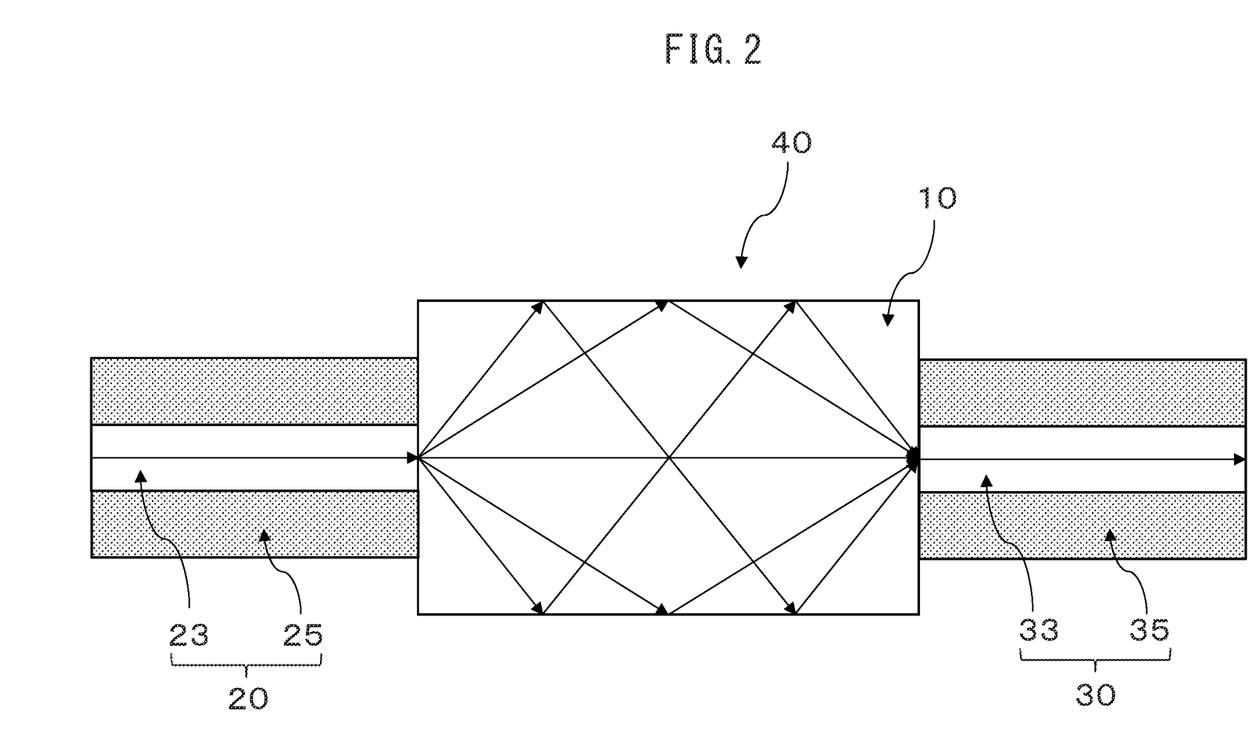
FIG. 2 is a schematic diagram showing an example of an optical fiber device that may be used in the method of the disclosure.

FIG. 2 is a schematic diagram showing an example of an optical fiber device that may be used in the method of the disclosure. The optical fiber device shown in FIG. 2 has a sensor unit 10 composed of a multimode fiber, and an incoming light fiber 20 and outgoing light fiber 30 composed of single-mode fibers, which are optically connected to the incoming light end and outgoing light end of the sensor unit 10, respectively. The incoming light fiber 20 has a core 23 and a cladding 25. The outgoing light fiber 30 also has a core 33 and a cladding 35. Liquid gasoline 40 is present on the outer side of the sensor unit 10. The diameter of the sensor unit 10 is larger than the diameters of the cores of the incoming light fiber 20 and outgoing light fiber 30.

In the optical fiber device shown in FIG. 2, incident light to the sensor unit 10 from the incoming light fiber 20 is diffracted in multiple directions, undergoing total reflection at the side walls of the sensor unit 10. Phase shifting by Goos-Hanchen shifting during total reflection depends on the refractive index of the sensor unit 10 and the refractive index of the gasoline on the outer side of the sensor unit. By using the optical fiber device shown in FIG. 2 it is possible to calculate the refractive index of liquid gasoline 40 by measuring the wavelength of light at which the phase just matches at the core 33 of the outgoing light fiber 30, as a value related to the refractive index.

<Step A1'>

In step A1', the proportion of the aromatic component concentration with respect to the sulfur component concentration in gasoline is lowered by removing a portion of the gasoline by gasification. Step A1' may be the same as step A1 described above.

<Step A2'>

In step A2', the sensor unit interior is irradiated with a laser from the incoming light fiber side, the wavelength of the irradiated laser is measured at the outgoing light fiber side, and a value related to the refractive index is measured based on the measured wavelength.

Measurement of the value related to the refractive index in step A2' can be carried out by referring to the measuring method with the optical fiber device described in PTL 1, except that the target of measurement is the liquid gasoline used in step A1'.

The laser irradiated into the sensor unit from the incoming light fiber side during measurement of the value related to the refractive index in step A2' may employ a laser of any desired wavelength that allows estimation of the sulfur component concentration in gasoline. More specifically, a laser with a wavelength in the range of 1500 nm to 1700 nm may be used.

<Method of Recovering Exhaust Gas Purifying Catalyst>

The method for recovering an exhaust gas purifying catalyst of the disclosure is a method of recovering an exhaust gas purifying catalyst that purifies exhaust gas emitted by an internal combustion engine in which gasoline is combusted, wherein the method comprises the following steps (A) to (C):

(A) estimating the sulfur component concentration in gasoline in the manner according to the disclosure, (B) estimating the estimated accumulated amount of sulfur oxides in the exhaust gas emitted by the internal combustion engine, based on the sulfur component concentration, and (C) recovering the exhaust gas purifying catalyst from the sulfur oxide-derived poisons when the estimated accumulated amount of discharged sulfur oxides is above a threshold value.

(Exhaust Gas Purifying Catalyst)

The exhaust gas purifying catalyst that may be used to carry out the method of recovering an exhaust gas purifying catalyst according to the disclosure may be any exhaust gas purifying catalyst that can produce catalyst poisoning by sulfur oxides such as $SO_X$ in exhaust gas. Such an exhaust gas purifying catalyst may be, but is not limited to, a $NO_X$ storage catalyst or three-way catalyst, for example.

(Step A)

Step A can be carried out by the method of estimating the concentration of sulfur components in gasoline according to the present disclosure.

(Step B)

In step B, the estimated accumulated amount of sulfur oxides in exhaust gas emitted by an internal combustion engine is estimated based on the sulfur component concentration. The estimated accumulated amount of sulfur oxides in exhaust gas emitted by the internal combustion engine can be estimated, for example, from the relationship between the sulfur component concentration in gasoline estimated in step A, and the amount of gasoline combusted by the internal combustion engine. More specifically, the product of the sulfur component concentration in gasoline and the gasoline combusted by the internal combustion engine may be used as the estimated accumulated amount of sulfur oxides. In step A, when a threshold value is used for estimation of the sulfur component concentration in gasoline and it is estimated that the sulfur component concentration in gasoline is above or within the threshold value, it may estimated whether the estimated accumulated amount is above or within a value corresponding to the threshold value for the sulfur component concentration in gasoline.

(Step C)

In step C, if the estimated accumulated amount of discharged sulfur oxides is above the threshold value, then treatment is carried out to recover the exhaust gas purifying catalyst from the sulfur oxide-derived poisons.

The relationship between the amount of $SO_X$ discharged from an internal combustion engine and catalyst poisoning of the exhaust gas purifying catalyst due to $SO_X$ is thought to differ depending on the type, structure and manner of usage of the exhaust gas purifying catalyst. Therefore, the reduction in exhaust gas purification efficiency of the exhaust gas purifying catalyst with respect to the estimated accumulated amount of sulfur oxides may be measured first, and the threshold value established as the estimated accumulated amount of sulfur oxides at the point where the exhaust gas purification efficiency has fallen below a level appropriately established by a person skilled in the art.

The "poisoning" of the exhaust gas purifying catalyst by sulfur oxides is reduction in the exhaust gas purification efficiency of the exhaust gas purifying catalyst by adhesion or absorption of the sulfur oxides in the exhaust gas purifying catalyst.

Treatment for recovery of the exhaust gas purifying catalyst from poisoning by sulfur oxides in step C may be carried out by any desired treatment method that allows sulfur oxides adhering to or stored in the exhaust gas purifying catalyst to be removed from the exhaust gas purifying catalyst. The treatment method may be carried out, for example, by heating the exhaust gas purifying catalyst to high temperature while using a high air/fuel ratio of the exhaust gas flowing into the exhaust purification catalyst.

EXAMPLES

Examples 1 and 2 and Comparative Example 1

Gasoline samples with benzothiophene concentrations of 1 ppm, 10 ppm, 100 ppm, 1000 ppm and 10,000 ppm were prepared to estimate sulfur concentrations in gasoline. For each of the prepared gasoline samples, the gasoline sample volatilization rate was changed as shown in Table 1 to measure the change in output of the optical fiber device at the different volatilization rates.

TABLE 1

| Example | Volatilization rate of gasoline sample (mass %) |
| --- | --- |
| Comparative Example 1 | 0 |
| Example 1 | 10 |
| Example 2 | 20 |

The optical fiber device used for measurement had the same construction as the optical fiber device described in detail for the estimating method of the disclosure. The optical fiber device therefore had a sensor unit composed of a multimode fiber, running through the gasoline sample, and an incoming light fiber and outgoing light fiber composed of single-mode fibers, which were optically connected to the incoming light end and outgoing light end of the sensor unit, respectively. The optical fiber device had the same material for the sensor unit and the cores of the incoming light fiber and outgoing light fiber, and the diameter of the sensor unit was larger than the diameters of the cores of the incoming light fiber and outgoing light fiber.

Light of wavelength 1520 nm to 1620 nm was supplied to the optical fiber device from an ASE light source, and the optical fiber device output was measured using an optical spectrum analyzer.

The optical fiber device was situated on a temperature adjustment plate and the temperature of the gasoline sample was kept at 25° C. during the measurement.

Figure 3:
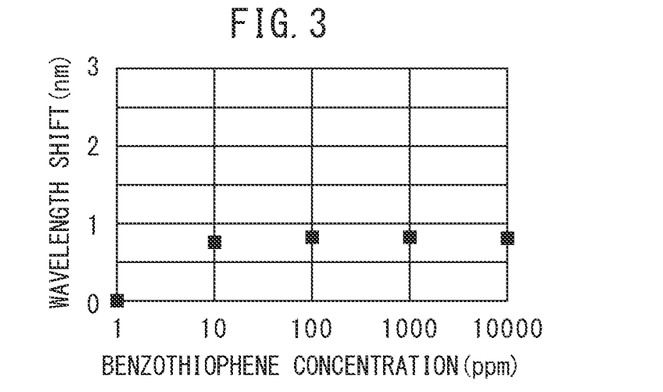
FIG. 3 is a graph showing the measurement results using an optical fiber device for different gasoline samples in Comparative Example 1.
Figure 4:
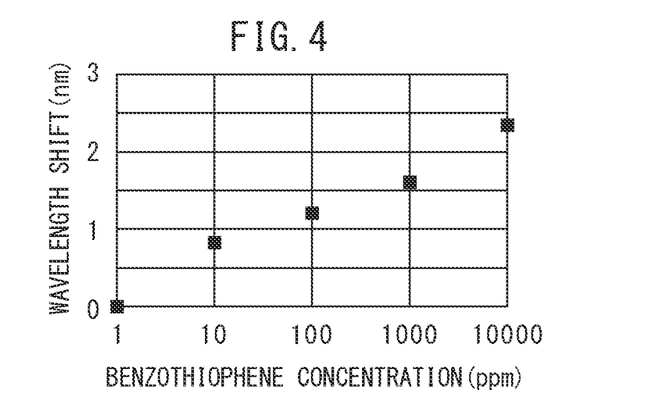
FIG. 4 is a graph showing the measurement results using an optical fiber device for different gasoline samples in Example 1.
Figure 5:
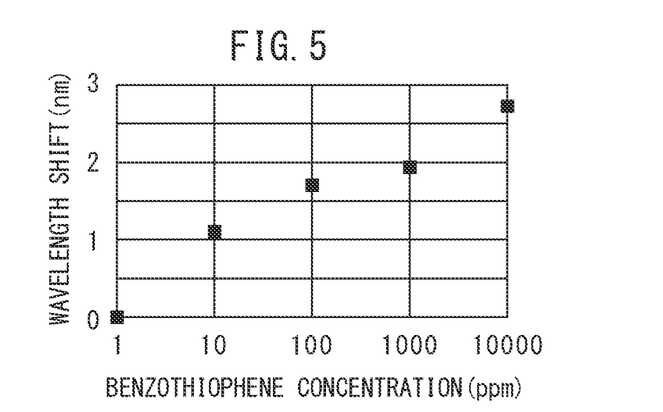
FIG. 5 is a graph showing the measurement results using an optical fiber device for different gasoline samples in Example 2.

The measurement results are shown in FIGS. 3 to 5. FIGS. 3 to 5 show the measurement results of gasoline samples using an optical fiber device, for Comparative Example 1, Example 1 and Example 2. In FIGS. 3 to 5, the abscissa represents benzothiophene concentration in the gasoline sample, and the ordinate represents wavelength shift. The wavelength shift is based on the measurement results for a gasoline sample with a benzothiophene concentration of 1 ppm.

When the gasoline sample volatilization rate was 0 mass %, i.e. when there was absolutely no gasification of the gasoline sample, as in Comparative Example 1, there was essentially no difference, with the sizes of the wavelength shift at benzothiophene concentrations of 10 ppm, 100 ppm, 1000 ppm and 10,000 ppm being all approximately 0.8 nm, as shown in FIG. 3.

In contrast, when the gasoline sample volatilization rate was 10 mass % as in Example 1, the wavelength shifts with benzothiophene concentrations of 10 ppm, 100 ppm, 1000 ppm and 10,000 ppm were about 0.8 nm, 1.2 nm, 1.6 nm and 2.4 nm, in that order, as shown in FIG. 4, and therefore the change in wavelength shift due to the benzothiophene concentration was considerable.

Even with a gasoline sample volatilization rate of 20 mass %, as in Example 2, the change in wavelength shift due to benzothiophene concentration was also considerable, as shown in FIG. 5, similar to Example 1.

This result suggests that when a gasoline sample has been volatilized, volatilization of the aromatic components that are major contributors to the refractive index of the gasoline sample reduces the concentration of aromatic components in the gasoline sample, thereby increasing the contribution by the benzothiophene content for the refractive index of the gasoline sample.

Reference Examples 1 to 8

Samples were prepared for Reference Examples 1 to 8 with the compositional ratios listed in Table 2, and the refractive index of each sample was measured.

TABLE 2

| | Sample composition (cc) | | | | Refractive index |
| --- | --- | --- | --- | --- | --- |
| Example | Benzothiophene | Toluene | Hexene | Hexane | |
| Reference Example 1 | 0.5 | 0.0 | 0.0 | 99.5 | 1.3661 |
| Reference Example 2 | 0.5 | 0.0 | 40.0 | 59.5 | 1.4098 |
| Reference Example 3 | 0.5 | 40.0 | 0.0 | 59.5 | 1.3707 |
| Reference Example 4 | 0.5 | 40.0 | 40.0 | 19.5 | 1.4165 |
| Reference Example 5 | 5.0 | 0.0 | 0.0 | 95.0 | 1.3714 |
| Reference Example 6 | 5.0 | 0.0 | 40.0 | 55.0 | 1.4153 |
| Reference Example 7 | 5.0 | 40.0 | 0.0 | 55.0 | 1.3764 |
| Reference Example 8 | 5.0 | 40.0 | 40.0 | 15.0 | 1.4212 |

A multiple regression formula was derived by the following procedure, based on the measurement results of the proportion of each component and the refractive index, for each of the samples of the reference examples. In formula (1), the amount (cc) in each sample is represented as $x_1$ for benzothiophene, $x_2$ for toluene and $x_3$ for hexene.

$$n = A \times x_1 + B \times x_2 + C \times x_3 + D \quad (1)$$

Defining the difference between the predicted value n and the measured value N for the refractive index as the residual error (e), the residual sum of squares Se is represented by the following formula (2).

[Mathematical Formula 1]

$$Se = \Sigma(N-n)^2 = E(N - A \times x_1 - B \times x_2 - C \times x_3 - D)^2 \quad (2)$$

The coefficients A, B, C and D were set so that Se=0, and the relationship between the gasoline refractive index and the aromatic component concentration (vol %) and sulfur component concentration (vol %) was determined, as represented by the following formula (3). In formula (3), (a) is the aromatic component concentration (vol %) and (b) is the sulfur component concentration (vol %).

$$N = 0.001 \times a + 0.001 \times b + 1.371 \quad (3)$$

As shown by formula (3), both the aromatic components and sulfur components contribute significantly to the refractive index of gasoline.

REFERENCE SIGNS LIST

10 Sensor unit
20 Incoming light fiber
23 Core
25 Cladding
30 Outgoing light fiber
33 Core
35 Cladding
40 Liquid gasoline

The invention claimed is:

1. A method for estimating the concentration of sulfur components in gasoline that contains sulfur components and aromatic components, wherein the method comprises:
   (A1) removing a portion of the gasoline by gasification to lower the proportion of the aromatic component concentration with respect to the sulfur component concentration in the gasoline,
   (A2) measuring values related to the refractive index of the gasoline, and
   (A3) estimating the sulfur component concentration in the gasoline based on the values related to the refractive index.

2. The method according to claim 1, wherein the method is performed by using, an optical fiber device which:
   has a sensor unit composed of a multimode fiber that runs through the gasoline, and
   has an incoming light fiber and outgoing light fiber composed of single-mode fibers, that are optically connected to an incoming light end and an outgoing light end of the sensor unit, respectively, wherein
   the sensor unit and cores of the incoming light fiber and outgoing light fiber are made of the same material, and
   the diameter of the sensor unit is larger than the diameters of the cores of the incoming light fiber and outgoing light fiber, and
   wherein in step (A2), the method comprises irradiating the sensor unit with a laser from the incoming light fiber side, measuring to m asure the wavelength of the irradiated laser from the outgoing light fiber side, and measuring the values related to the refractive index based on the measured wavelength.

3. The method according to claim 2, wherein a portion of the gasoline is removed by gasification in step (A1) by irradiating an interior of the sensor unit interior is irradiated with a laser from the incoming light fiber side to heat the gasoline and gasify a portion of the gasoline.

4. The method according to claim 1, wherein in step (A1), the gasoline is heated to gasify a portion of the gasoline.

5. The method according to claim 1, wherein the sulfur components comprise dimethylthiophene, dibenzothiophene, benzothiophene or any combination of the same.

6. The method according claim 1, wherein the aromatic components comprise toluene.

7. A method for recovering an exhaust gas purifying catalyst that purifies exhaust gas emitted by an internal combustion engine in which gasoline is combusted, wherein the method comprises:
   (A) estimating the sulfur component concentration in the gasoline by the method according to claim 1,
   (B) estimating an estimated accumulated amount of sulfur oxides in the exhaust gas emitted by the internal combustion engine, based on the sulfur component concentration, and
   (C) recovering the exhaust gas purifying catalyst from sulfur oxide-derived poisons when the estimated accumulated amount of discharged sulfur oxides is above a threshold value,
   wherein a reduction in exhaust gas purification efficiency of the exhaust gas purifying catalyst with respect to the estimated accumulated amount of sulfur oxides is measured first, and the threshold value is established as the estimated accumulated amount of sulfur oxides at the point where the exhaust gas purification efficiency has fallen below a predetermined level.

* * * * *